US00PP13485P2

(12) United States Plant Patent
Utecht

(10) Patent No.: US PP13,485 P2
(45) Date of Patent: Jan. 21, 2003

(54) GERANIUM PLANT NAMED 'FISROSIMO'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/323,108

(22) Filed: Jun. 1, 1999

(51) Int. Cl.[7] ..... A01H 5/00
(52) U.S. Cl. ..... Plt./325
(58) Field of Search ..... Plt./325, 328, 329, Plt./327

(56) References Cited

FOREIGN PATENT DOCUMENTS

| | | |
|---|---|---|
| PL | 473 | 12/1998 |
| CA | 98-1365 | 4/1998 |
| CH | 98-26-1432 | 4/1998 |
| DE | PEL 1363 | 9/1996 |
| EP | 97/0961 | 9/1997 |

OTHER PUBLICATIONS

Pelargonium 1998, Pelfi Fischer, Hillscheid Germany, p. 7 (1998/1999).

Licensing agreement for 'Fisrosimo', http://www.sicasov.com/baremes/f–f9899.htm, 1998/1999.*

Kessler, Greenhouse Production of Zonal Geranium, http://www.aces.edu/department/extcomm/publications/anr/anr–1106/anr–1106.htm, Apr. 1998.*

UPOV–ROM GTIM Computer Database 1999/02, GTI Jouve Retrieval Software, citation for 'Fisrosimo', 1996–1998.*

* cited by examiner

*Primary Examiner*—Bruce R. Campell
*Assistant Examiner*—Anne Marie Grünberg
(74) *Attorney, Agent, or Firm*—Foley & Lardner

(57) ABSTRACT

A new and distinct cultivar of geranium plant named 'Fisrosimo', as described and illustrated, and particularly characterized by the combined features of light pink flowers with large rose eyes; uniform dark-green foliage; compact plant habit; fairly early spring flowering response; and rich flowering throughout the summer.

1 Drawing Sheet

BACKGROUND OF THE INVENTION

The present invention comprises a new and distinct cultivar of geranium plant, botanically known as *Pelargonium zonale*, and hereinafter referred to by the cultivar name 'Fisrosimo'.

'Fisrosimo' is a product of a planned breeding program which had the objective of creating geranium cultivars with single or semi-double flowers with distinct 'eyes' in combination with dark green foliage.

'Fisrosimo' was originated from a hybridization made by the inventor, Angelika Utecht, in a controlled breeding program in Galdar, Gran Canaria, Spain, in 1993. The female parent was the variety 'Icecrystal' (unpatented), having light violet, semi-double flowers with rose-red to purple eyes, relatively large, grass-green leaves without zonation, and medium tall plant habit. The male parent of 'Fisrosimo' was a hybrid seedling, designated no. 508/6, which was characterized by single white flowers with large pink eyes, dark green foliage without zonation, and relatively compact habit. Hybrid seedling no. 508/6 was derived from crossings of a tetraploid line of 'Stadt Bern' (unpatented, commercial variety with very dark-green foliage) with white-flowering seedlings (proprietary breeding lines/plant material).

'Fisrosimo' was selected as one flowering plant within the progeny of the stated cross by the inventor, Angelika Utecht, in 1994 in a controlled environment in Galdar, Gran Canaria, Spain.

The first act of asexual reproduction of 'Fisrosimo' was accomplished when vegetative cuttings were taken from the initial selection in autumn 1994 in a controlled environment in Galdar, Gran Canaria, Spain by Angelika Utecht. Horticultural examination of plants grown from these cuttings, initiated in May 1995 in Hillscheid, Federal Republic of Germany, and continuing thereafter, has demonstrated that the combination of characteristics as herein disclosed for 'Fisrosimo' are firmly fixed and are retained through successive generations of asexual reproduction.

BRIEF DESCRIPTION OF THE INVENTION

The following traits have been repeatedly observed and are determined to be basic characteristics of 'Fisrosimo', which in combination distinguish this geranium as a new and distinct cultivar:

1. Weakly semi-double, light pink flowers with distinct rose eyes;
2. Very large umbrella-shaped inflorescence;
3. Uniform, dark-green colored foliage without zonation;
4. Moderately compact, uniformly-shaped and well-branched plant habit; and
5. Early to medium flowering response.

'Fisrosimo' has not been observed under all possible environmental conditions. The phenotpye of the new cultivar may vary significantly with variations in environment such as temperature, light intensity and daylength without any change in the genotype of the plant. The following observations, measurements, and comparisons describe plants grown in Hillscheid, Germany, and in Langley, Bristish Columbia, Canada, under greenhouse conditions which approximate those generally used in commercial practice.

Of the many commercial cultivars known to the present inventor, the most similar in comparison to 'Fisrosimo' is the variety 'Fisbravo' (U.S. Plant Pat. No. 9,765). In comparison to 'Fisbravo', 'Fisrosimo' has a somewhat lighter and slightly more bluish main flower color, smaller, but more distinct rose eyes on its petals, larger and differently shaped umbels, and foliage without zonation.

BRIEF DESCRIPTION OF THE DRAWING

The accompanying color photographic drawing shows typical flower and foliage characteristics of 'Fisrosimo' with colors being as true as possible will illustrations of this type.

DETAILED BONTANICAL DESCRIPTION

The measurements were taken in Langley, British Columbia, Canada, on May 26, 1998, 10 weeks after planting of rooted cuttings into 15-cm pots. The plants had not been pinched. In the following description, color references are made to The Royal Horticultural Society Colour Chart (R.H.S.). The color values were determined indoors from flowers developed in a greenhouse in May 1998 in Hillscheid, Germany.

CLASSIFICATION

Botanical: A hybrid of the species *Pelargonium zonale L'Hérit.*

Commercial: Zonal geranium, cv. 'Fisrosimo'.

INFLORESCENCE

Umbel:

*Shape.*—Flat and wide, umbrella-shaped.

*Average diameter.*—124 mm.

*Average depth.*—45 mm.

*Peduncle length.*—119 mm.

*Peduncle texture.*—Slightly velvety due to pubescence.

*Peduncle color.*—Bright green, RHS 143 A, slight infusion with anthocyanin may occur creating an olive-green, RHS 146 A, to slight rust coloring, near RHS 173 A.

*Pedicel length.*—31 mm.

*Pedicel color.*—Green to light red at the middle part.

*Number of flowers per umbel.*—Approximately 25–30.

*Lastingness of the individual umbel.*—Wide with individual flowers in various stages of development; persistence is above average for zonal varieties, umbel lasting approximately 15 days in greenhouse conditions in spring at a minimum temperature of approximately 18° C.

Corolla:

*Average diameter.*—48 mm.

*Form.*—Weakly semi-double, appearance like single-form.

*Shape.*—Flat, cup-shaped and nearly round.

*Average number of petals.*—5.6.

*Number of petaloids.*—0 or 1.

*Color (general tonality from a distance of three meters).*—Very light purple-pink with large rose eyes.

*Color of upper petals.*—RHS 73 D, which includes the margin.

*Markings of upper petals.*—RHS 57 C, with rose/purple-pink eye, and white zone at the base.

*Color of lower petals.*—RHS 75 C, which includes the margin.

*Markings of lower petals.*—RHS 57 B, with rose/purple-pink eye, the markings are somewhat smaller than those on the upper petals.

*Color of lower surface of petals.*—Approximately RHS 69 A.

*Color of sepals.*—Mainly light to medium green, RHS 143 B, slightly reddish at the base.

*Number of sepals.*—5.

*Sepal texture.*—Slightly velvety due to pubescence.

Bud (immediately before unfolding of the petals):

*Shape.*—Narrow and elliptical.

*Color (sepals).*—Light green, RHS 143 C, small reddish spot at the base.

*Color (petals).*—Light violet-pink, approximately RHS 70 C, variable.

*Length.*—Approximately 20 mm.

*Width.*—Approximately 11 mm.

Reproductive organs:

*Androecium.*—7 fertile anthers, white filaments, yellow-orange pollen.

*Gynoecium.*—5–6-lobed stigma, light pink style and stigma, approximately RHS 65 A.

*Fertility/seed set.*—Natural seed set, without artificial pollination, may occur in late summer to autumn.

Spring flowering response period: In Hillscheid, Germany, in 1998, plants had on average 0.7 flowers opened 12 weeks after planting of unrooted cuttings.

Outdoor flower production: Very floriferous, even though the inflorescence is large.

*Blooming habit.*—Continuous flowering from about May to mid-September; after which flowering may be poor depending on general conditions and light intensity. There is no noticeable fragrance apart from the slightly aromatic scent that can be noticed when flowers are crushed.

*Lastingness of the individual bloom.*—Under rainy conditions lasts longer than other varieties, the flowers last approximately 8 days in greenhouse conditions in spring at a minimum temperature of approximately 18° C.

Durability: Fair shatter resistance, relatively good rain resistance.

PLANT

Foliage:

*Form.*—Kidney-shaped with only weak lobes, and with slightly open base.

*Margin.*—Bicrenated, wavy.

*Texture.*—Lower surface is slightly velvety due to pubescence and smooth apart from protruding veins; upper surface is smooth, slightly dull.

*Size of leaf.*—76 mm.

*Color of upper surface.*—Medium to dark green, approximately RHS 137 B.

*Color of lower surface.*—RHS 137 C.

*Color of zonation.*—Usually no zonation.

*Tolerance of botrytis.*—Average.

General appearance and form:

*Internode length.*—10 mm.

*Branching pattern.*—5.9 naturally-occurring branches.

*Size of foliage.*—13.5 cm high and 26.0 cm in diameter.

I claim:

1. A new and distinct cultivar of geranium plant named 'Fisrosimo', as described and illustrated.

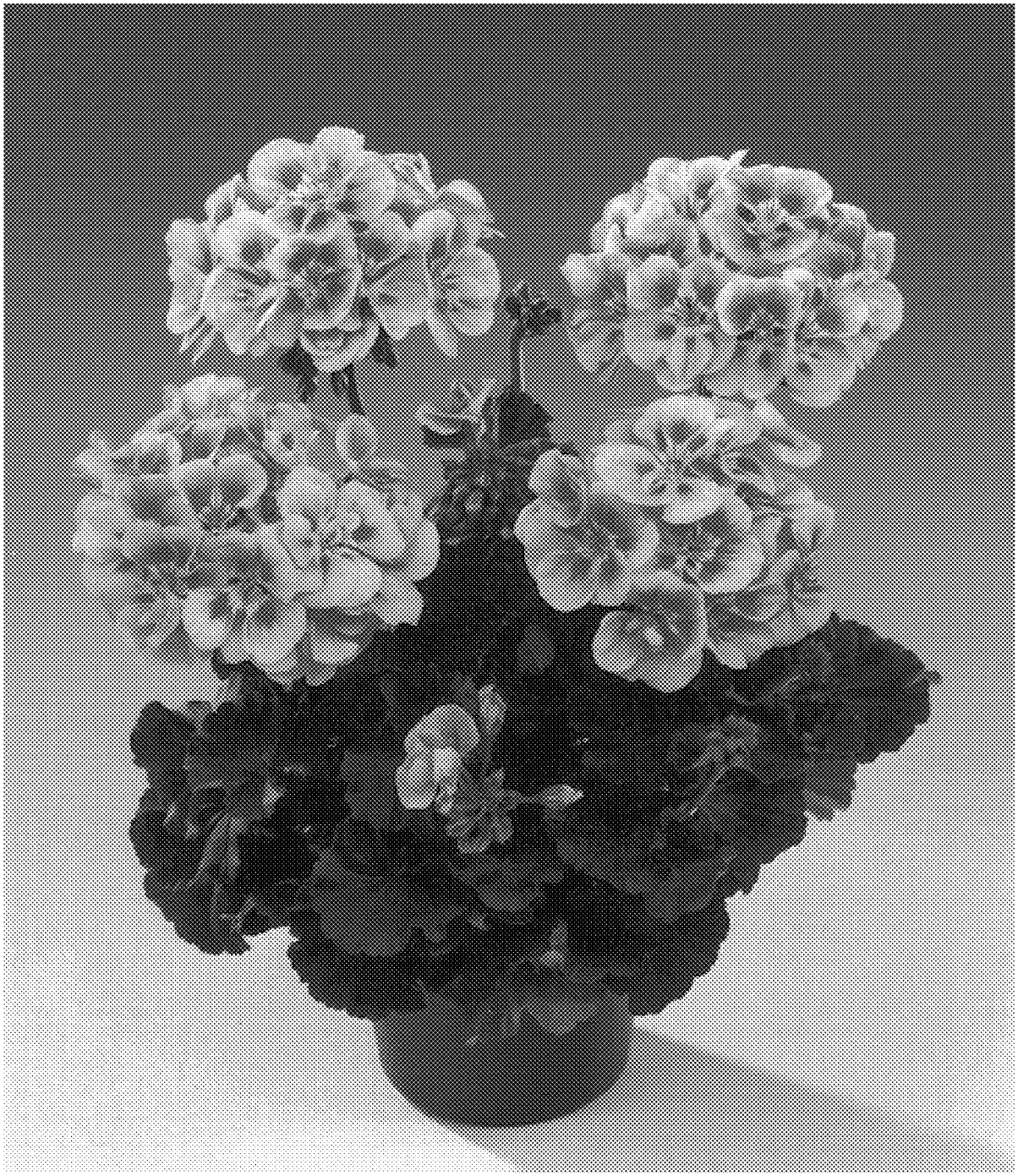

* * * * *